United States Patent [19]

Haber et al.

[11] Patent Number: 4,584,990

[45] Date of Patent: Apr. 29, 1986

[54] PROSTHETIC SPHINCTER HAVING A DIAMETRIC OCCLUSION GEOMETRY

[75] Inventors: Terry M. Haber, Lake Forest; William H. Smedley, Lake Elsinore; Clark B. Foster, Irvine, all of Calif.

[73] Assignee: Habley Medical Technology Corporation, Laguna Hills, Calif.

[21] Appl. No.: 656,980

[22] Filed: Oct. 2, 1984

[51] Int. Cl.$^4$ ............................................. A61B 19/00
[52] U.S. Cl. .......................... 128/1 R; 128/DIG. 25; 128/325
[58] Field of Search ............... 128/1 R, DIG. 25, 325, 128/346; 604/97

[56] References Cited

U.S. PATENT DOCUMENTS

| | | | |
|---|---|---|---|
| 2,756,753 | 7/1956 | Means | 128/DIG. 25 |
| 3,730,186 | 5/1973 | Edmunds et al. | 128/DIG. 25 |
| 3,741,216 | 6/1973 | Vosowitz et al. | 128/346 |
| 3,744,063 | 7/1973 | McWhorter et al. | 128/346 X |
| 4,019,499 | 4/1977 | Fitzgerald | 128/DIG. 25 |
| 4,222,377 | 9/1980 | Burton | 128/DIG. 25 |
| 4,346,869 | 8/1982 | MacNeill | 128/346 X |
| 4,399,809 | 8/1983 | Baro et al. | 128/DIG. 25 |
| 4,419,985 | 12/1983 | Trick | 128/DIG. 25 |
| 4,428,365 | 1/1984 | Hakky | 128/1 R |

Primary Examiner—Edward M. Coven
Attorney, Agent, or Firm—Morland C. Fischer

[57] ABSTRACT

An elastofluidic sphincter comprising a prosthetic device for surgical implantation around a patient's lumen, such as the urethra. The sphincter includes an occlusion cuff which is positioned to surround and engage the patient's lumen for occluding or relaxing the lumen to achieve coaptation for the treatment of incontinence. The occlusion cuff includes hollow, expandable patient activated and physician controlled chambers arranged to generate diametric occlusive pressures for efficiently occluding the lumen with precise and minimal pressure, so as to minimize the interruption of circulatory blood flow. Expansion of the patient and physician chambers is independently and selectively controlled by the patient and physician, respectively, whereby to precisely and continuously adjust the occlusive pressures applied from the occlusion cuff to the lumen. The sphincter includes a pressure relief ring which may be manually operated, while in situ, to cause the patient activated chamber to shrink, whereby to reduce the occlusive pressures being applied to the lumen for maximizing the movement of material and circulatory blood flow therethrough.

11 Claims, 14 Drawing Figures fig 5 fig 6 fig 7 fig 8 fig 9 fig 10 fig 11 fig 12 fig 13 fig 14

PROSTHETIC SPHINCTER HAVING A DIAMETRIC OCCLUSION GEOMETRY

BACKGROUND OF THE INVENTION

1. Field of the Invention

This invention relates generally to prosthetic devices and, more particularly, to an artificial prosthetic sphincter for surgical implantation, whereby to overcome the problem of incontinence. The present sphincter represents an improvement in the construction of a prosthetic sphincter so as to be characterized by a diametric occlusion geometry capable of occluding a lumen, such as the urethra, with greater efficiency, improved biocompatability, less complex implant surgery, and easier and more precise post-surgical occlusive pressure adjustment than that which has characterized prosthetic sphincters of the prior art.

2. Prior Art

As will be recognized by those skilled in the art, certain individuals, because of a disability or surgical procedure or other organic and/or phychogenic cause, do not possess adequate function or competence of various bodily organs or muscles so as to achieve natural sphincteric continence for controlling the involuntary passage of urine. Accordingly, many sphincteric mechanisms have been proposed for surgical implantation as part of a system to selectively occlude and relax a lumen, such as the urethra, for controlling the passage of material therethrough. However, most known sphincteric mechanisms are characterized by a common shortcoming. That is, once the implant surgery is completed, there is no readily available means (without necessitating additional surgery) to accurately and continuously adjust the occlusive pressures to be applied to the urethra, or other lumen, to achieve continence.

More particularly, because of the swollen and aggravated condition of edema of the urethral tissues during and for a period subsequent to surgery, the physician cannot be certain as to the normalized condition of the patient's urethra until post-operative edema has subsided. Therefore, the physician must estimate the required minimal occlusive force needed to achieve coaptation. As a consequence of such estimate, sphincteric mechanisms are often improperly fitted or selected, so that the maximum occlusive pressure capability of such mechanisms is insufficient to successfully achieve continence or the minimum occlusive pressure capability exceeds the pressure needed to achieve continence. Excessive occlusive forces are known to undesirably minimize arteriovascular blood flow to the urethra and thereby increase the possibility of ischemia and erosion to the delicate tissues.

Moreover, where conventional sphincteric mechanisms include occlusive force control means, such force control is usually accomplished in large, step-wise increments. Therefore, no artificial sphincters are known which are adapted to easily and accurately control or continuously vary the occlusive pressures needed to achieve continence, so that the sphincter may be percutaneously tailored to the individual needs of the patient on an ongoing basis without requiring additional surgery.

What is still more, many conventional sphincteric mechanisms are characterized by a circumferential occlusion geometry. It has been found, and as will be pointed out in greater detail below, that sphincters which apply circumferential occlusive pressures to occlude the urethra are comparatively inefficient and must generate considerably greater pressures to achieve minimal coaptive continence (relative to a diametric occlusion geometry, as is characteristic of the sphincter of the present invention). In addition, it is believed that circumferential occlusive forces tend to increase the susceptibility of the urethra to atrophy, erosion, and/or ischemia.

SUMMARY OF THE INVENTION

Briefly, and in general terms, an artificial prosthetic sphincter is disclosed for surgical implantation. The sphincter includes an occlusion cuff which is positioned to surround and engage a patient's lumen (e.g. urethra) and adapted to generate sufficient occlusive pressures to achieve coaptation and thereby overcome incontinence. The occlusion cuff includes a pair of oppositely disposed, inflatable patient activated and physician controlled chambers. Each of the patient activated and physician controlled chambers is interfaced with a respective and independent patient or physician operated fluid circuit, whereby a fluid medium can be selectively supplied to one or both of the chambers for causing expansions thereof and an increase in the occlusive pressures applied to the lumen. By virtue of the oppositely disposed patient and physician chambers, the occlusion cuff is advantageously characterized by a diametric occlusion geometry by which minimal diametric occlusive pressures are applied to the lumen to more effectively and efficiently achieve coaptation with a reduced possibility of atrophy, erosion and/or ischemia (relative to a conventional circumferential occlusion geometry).

In a preferred embodiment of the invention, the occlusion cuff is surgically positioned around the bulbous urethral portion of the corpus spongiosum. The patient operated fluid circuit extends from the patient activated chamber at the occlusion cuff to a palpable, loose skin area at the posterior superior aspect of the scrotum, where it may be manipulated by the patient to supply fluid to and thereby inflate the patient activated chamber for providing occlusive pressures to the lumen. The physician operated fluid circuit extends from the physician controlled chamber at the occlusion cuff to the aforementioned palpable, loose skin area where it is conveniently accessible solely to the physician by means of a fluid containing syringe. In the event that the occlusive pressure generated by the patient activated chamber is insufficient to achieve coaptation, the physician may continuously and accurately increase the application of occlusive pressure to the lumen by inserting a syringe into the physician operated fluid circuit so as to supply fluid to and thereby inflate the physician controlled chamber. Thus, by virtue of the present invention, the physician may selectively adjust the occlusive forces being generated by the physician controlled chamber without subjecting the patient to additional surgery, so that the sphincter can be individually customized to generate the minimum total occlusive pressures required by the patient to achieve coaptive continence.

The patient operated fluid circuit also includes a pressure relief ring associated therewith. In the event that the patient should experience a temporary return of natural continence, the pressure relief ring may be manually operated, while in situ, to cause the patient activated chamber to shrink, whereby to reduce the occlusive pressures being applied to the lumen for maximizing the movement of material and blood flow therethrough.

DESCRIPTION OF THE PREFERRED EMBODIMENT

Figures 1, 2, 3, 4:
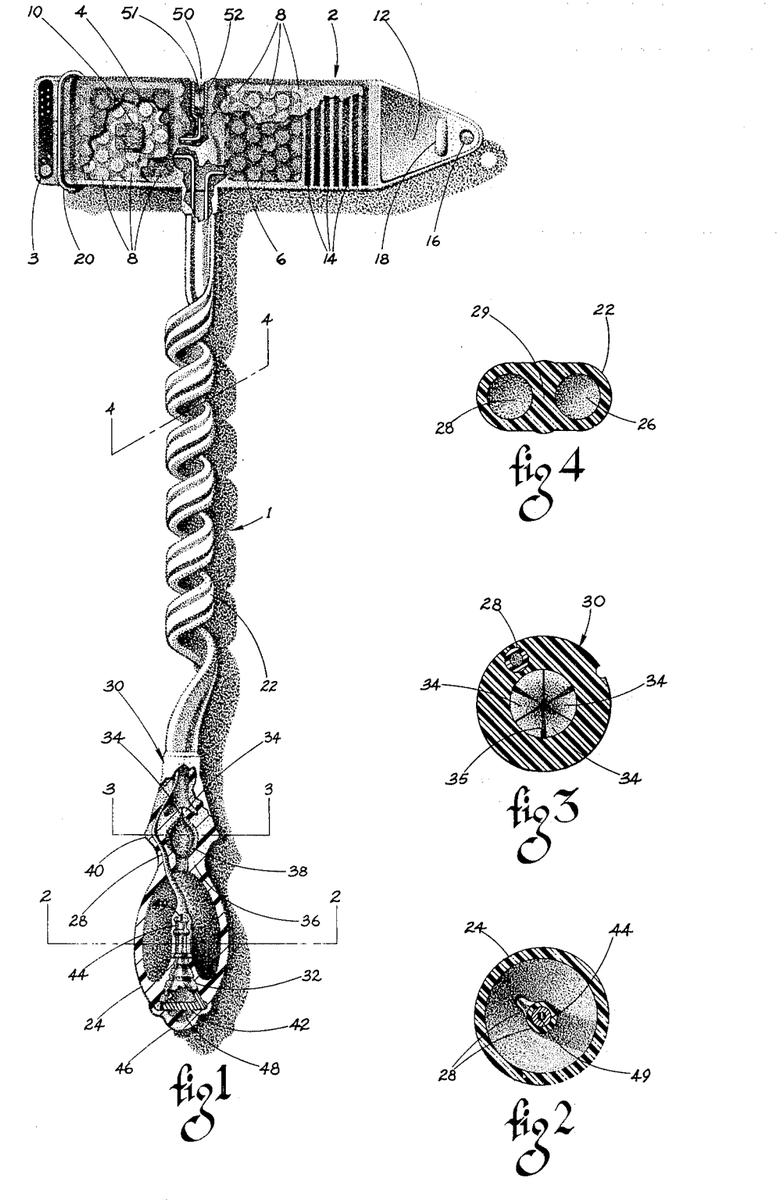
FIG. 1 is an elevational view, partially broken away, of the elastofluidic sphincter which forms the present invention.
FIG. 2 is a cross-section taken along lines 2—2 of FIG. 1.
FIG. 3 is a cross-section taken along lines 3—3 of FIG. 1.
FIG. 4 is a cross-section taken along lines 4—4 of FIG. 1.

Referring concurrently to FIGS. 1-4 of the drawings, a elastofluidic sphincter 1 is shown having a unique occlusive pressure delivery and variation system which is adapted to be tailored to the tissue requirements of the patient. Sphincter 1 has particular application to a patient having physiological or neurological itiology which may require that occlusive pressures be occasionally and variably generated to achieve continence. Sphincter 1 is preferably fabricated from a biocompatible, elastomeric, cross-linked polymer material, such as silicone, polyurethane, or the like, having a spring-like memory. As is best shown in FIG. 1, sphincter 1 includes a generally flat occlusion cuff 2 located at one end thereof. Occlusion cuff 2 includes an X-ray opaque serialization insert 3 fabricated from gold, platinum, tantalum, or the like, to provide suitable identifying indicia for manufacturing traceability and quality assurance. As will be disclosed in greater detail when referring to FIGS. 7-9, hereinafter, occlusion cuff 2 may be suitably positioned by a physician during implant surgery so as to surround and articulate a patient's lumen (e.g. urethra) to selectively and variably control occluding and relaxing the lumen to promote or obturate the movement of material therethrough.

Occlusion cuff 2 includes a pair of oppositely disposed hollow, expandable chambers 4 and 6 which, as will soon be described, are adapted to be filled with a force transmitting medium to cause the inflation thereof and a corresponding increase in the occlusive pressures generated against the patient's lumen. For reasons which will soon become apparent, chamber 4 is referred to as the patient activated chamber and chamber 6 as the physician controlled chamber.

Extending from the surface of occlusion cuff 2 in a direction so as to engage the patient's lumen when cuff 2 is positioned therearound is a matrix of protuberances or bumps 8. The protuberances 8 act as pressure transmitting points to transmit occlusive pressures from the cuff 2 to the lumen, whereby to achieve coaptation (i.e. closure of the lumen). The relatively flat regions of occlusion cuff 2 which surround protuberances 8 minimize the application of occlusive pressures to axial and lateral blood vessels which nourish the lumen, so as to maximize freedom of arteriovascular blood flow and reduce the possibility of ischemia and erosion to the delicate tissues.

Located at the interior of each of the patient activated and physician controlled chambers 4 and 6 and bonded to the opposite faces thereof is at least one extensible, tensile resistant webbing (only one of which 10 being shown for convenience). The advantage provided by webbing 10 during the inflation of chambers 4 and 6 will be described hereinafter when referring to FIGS. 5 and 6 of the drawings.

A tapered distal aspect 12 of solid cross section is coextensively formed with occlusion cuff 2 at one end thereof. Extending from the surface of occlusion cuff 2 in a direction opposite the matrix of protuberances 8 is a series of locking ridges 14 (best illustrated in FIGS. 7-9). The location of ridges 14 is preferably confined to a surface region of cuff 2 between the distal aspect 12 and the physician controlled chamber 6. The distal aspect 12 of cuff 2 has an aperture 16 extending therethrough. Aperture 16 is suitably sized to receive therein either an umbilical, a suture, a tool, or the like, whereby to permit the physician to conveniently position occlusion cuff 2 around the patient's lumen. Distal aspect 12 also includes a raised safety stop 18 extending upwardly therefrom.

Extending through the end of occlusion cuff 2 opposite distal aspect 12 is an adjusting clip 20. The physician may secure the occlusion cuff 2 around the patient's lumen (best described while referring to FIGS. 7-9) by fitting the distal aspect 12 through the adjusting clip 20 such that the clip is received between a pair of successive locking ridges 14. In the event that a repositioning of the adjusting clip 20 should become necessary during implant surgery, the raised safety stop 18 advantageously provides means by which to prevent the accidental disengagement of occlusion cuff 2 from the patient's lumen.

A connecting channel 22 of sphincter 1 extends between occlusion cuff 2 and a bulb or reservoir 24 containing a force transmitting medium. By way of example, the force transmitting medium may be a gel, a silicone lubricating fluid, Iothalamate solution, a saline solution, or any other suitable low compressibility material. Connecting channel 22 functions as a conduit to permit the force transmitting medium to be selectively supplied to the patient activated and/or physician controlled chambers 4 and 6. Connecting channel 22 is fabricated as a continuous series of extensible, shock absorbing, helically wound rings which provide both a force damping characteristic to insulate delicate luminal tissue and an inherent length adjustment to accommodate post-operative patient movement after sphincter implantation. Moreover, the compression resistant cross section (designated 29 in FIG. 4) of channel 22 prevents a kinking of the helical rings which could result in an undesirable interruption in the supply of force transmitting medium between reservoir 24 and occlusion cuff 2.

As is best shown in FIG. 4 of the drawings, a pair of patient activated and physician controlled tubes 26 and 28 extend through connecting channel 22. The patient activated tube 26 communicates between the reservoir 24 of force transmitting medium and the patient activated chamber 4 at occlusion cuff 2 by way of a monolithic pressure stabilizing chamber 30. The physician controlled tube 28 communicates between a needle directing insert 32 (disposed securely within reservoir 24) and the physician controlled chamber 6 at occlusion cuff 2.

The structure and operation of pressure stabilizing chamber 30 have been previously disclosed in detail in U.S. patent application Ser. No. 574,596, filed Jan. 27, 1984. Nevertheless, a brief description of chamber 30 is provided hereat while referring to FIGS. 1 and 3 of the drawings. Pressure stabilizing chamber 30 is located within sphincter 1 between the proximal end of connecting channel 22 and reservoir 24. Chamber 30 includes a suitable plurality of arcuately shaped flow control appendages 34 that are uniformly spaced in a normally closed position across chamber 30 so as to prevent the movement of force transmitting medium between reservoir 24 and patient activated tube 26. That is, in the normally closed position of FIG. 3, appendages 34 extend towards and engage one another to block the flow of force transmitting medium therepast. Extending laterally through the pressure stabilizing chamber 30 between reservoir 24 and flow control appendages 34 is a flexible and hollow force transmitting body 36. Force transmitting body 36 is spaced from the walls of chamber 30 by longitudinally extending vanes or flutes 35. Force transmitting body 36 includes a bulbous portion 38 of relatively large diameter. Bulbous portion 38 has a tapering portion which terminates at the interface of flow control appendages 34. Molded into the exterior of sphincter 1 around the outside diameter of pressure stabilizing chamber 30 adjacent the location of bulbous portion 38 is a pressure relief ring 40. Pressure relief ring 40 is of suitable size and shape to receive the thumb and index finger of the patient or physician to perform a function that will be described in greater detail hereinafter.

The details of needle directing insert 32 are now disclosed while referring to FIGS. 1 and 2 of the drawings. As previously indicated, insert 32 is located at the interior of reservoir 24. Insert 32 is preferably fabricated from an alloy of cobalt and chromium, titanium, stainless steel, or any other suitable biocompatible, structurally sound and non-corrosive material. Insert 32 comprises a hollow and generally conical base portion 42 and a tubular end portion 44 coextensively formed with base portion 42 so that a continuous fluid path is established through insert 32. In the assembled sphincter relationship, the conical base portion 42 of needle directing insert 32 functions as a syringe docking port and is located at approximately the center of the proximal end of reservoir 24 immediately adjacent a subcutaneous locating nodule 46. Locating nodule 46 may be formed of relatively high durometer silicone. A suitable healing gel 48 (e.g. silicone, or the like) is disposed between the conical end 42 of insert 32 and the locating nodule 46. The tubular end 44 of insert 32 is interconnected with the proximal end of physician controlled tube 28. Tubular end 44 is of suitable dimension to form a safety stop 49 for any syringe inserted therein. More particularly, and as will soon be disclosed in greater detail, an external supply of force transmitting medium may be supplied to physician controlled tube 28 by means of a syringe (not shown). The syringe is inserted by the physician through nodule 46, healing gel 48, and the conical docking and tubular end portions 42 and 44 of insert 32. Safety stop 49 blocks the penetration of the syringe beyond tubular insert end 44, so as to prevent damage to (and possible leakage from) physician controlled tube 28. When the syringe is withdrawn from insert 32, the gel 48 acts to heal and seal the locating nodule 46 so as to prevent damage (and possible leakage) caused by any remaining puncture wound.

As an important feature of the present invention and as illustrated FIG. 1, patient and physician circuits are formed through sphincter 1, whereby a patient and/or a physician may selectively introduce a supply of force transmitting medium into the patient activated and physician controlled chambers 4 and 6, respectively, to inflate such chambers and thereby cause a corresponding and proportional increase in the occlusive pressures transmitted to the patient's lumen from occlusion cuff 2. That is, the patient circuit comprises reservoir 24, pressure stabilizing chamber 30, patient activated tube 26, and patient activated chamber 4. The physician circuit comprises needle directing insert 32, physician controlled tube 28, and physician controlled chamber 6. While the physician circuit is initially devoid of force transmitting medium, the patient circuit (at reservoir 24) is initially filled with a pre-measured volume of such medium during sphincter manufacture.

The initial filling of reservoir 24 is accomplished by way of a needle entry port 50 conveniently located within occlusion cuff 2. Entry port 50 preferably comprises a hollow, metallic (e.g. titanium, or the like) insert which communicates with the patient activated chamber 4 via a healing and sealing gel 51 and a syringe safety stop 52 which are similar to the gel 48 and safety stop 49 previously disclosed when referring to needle directing insert 32. During sphincter manufacture, the reservoir bulb 24 is compressed and a syringe (not shown) is inserted into entry port 50 so as to introduce a supply of force transmitting medium to patient activated chamber 4. The reservoir bulb 24 is thereupon caused to expand back to its original, non-compressed shape (by means of operating pressure relief ring 40, in a manner that will soon be described), whereby the combination of the resulting suction force and the energy stored in distended patient activated chamber 4 cooperatively draws force transmitting medium from chamber 4 to reservoir 24 by way of patient activated tube 6 without the aid of a separate pump, as is undesirably common to some conventional sphincteric mechanisms. After reservoir 24 has been filled with a suitable supply of force transmitting medium, the sphincter 1 is suitable for implantation to permit continence to be achieved by selectively varying the occlusive pressures applied to the patient's lumen from occlusion cuff 2.

Figure 5:
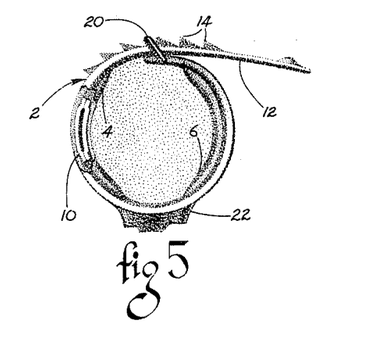
FIG. 5 is an end view of the sphincter of FIG. 1 in an uninflated condition.
Figure 6:
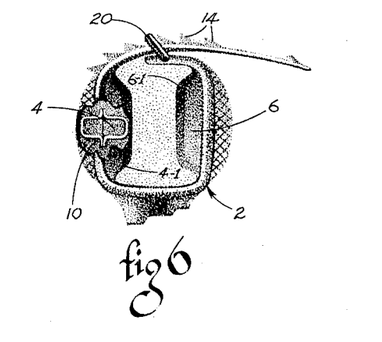
FIG. 6 is an end view, partially broken away, of the sphincter of FIG. 1 in an inflated condition.

The operation of sphincter 1 is now diclosed while referring concurrently to FIGS. 1, 5, and 6 of the drawings. As previously indicated, during implant surgery, the physician secures occlusion cuff 2 around the patient's lumen so that the matrix of pressure transmitting protuberances (designated 8 in FIG. 1) engage the lumen. That is, the tapered distal aspect 12 of cuff 2 is inserted through and pulled past adjusting clip 20 until clip 20 is received between a pair of locking ridges 14. The physician may pull distal aspect 12 through clip 20 until the circumference of occlusion cuff 2 is particularly adjusted to suitably fit around the patient's lumen.

The receipt of clip 20 between ridges 14 prevents occlusion cuff 2 from becoming accidentally loosened from its fit around the lumen.

A preferred location for positioning sphincter 1 in order to occlude and relax the patient's lumen (e.g. urethra) includes surrounding the bulbous urethral portion of the corpus spongiosum (not shown) with occlusion cuff 2. However, it is to be understood that the lumen to be surrounded by occlusion cuff 2 may also be the intestine, the esophagus, an artery, a vein, or the vas deferins. After implant, connecting channel 22 extends into the patient's scrotum, such that the reservoir 24 of force transmitting medium and pressure relief ring 40 are located at a palpable, loose skin area at the posterior superior aspect of the scrotum. Thus, the reservoir 24 and pressure relief ring 40 may be suitably and accessibly located so as to minimize the possibility of patient discomfort while allowing the patient to manipulate the sphincter 1 in a manner to be disclosed below.

To achieve continence after the passage of a suitable sphincter dormancy period following implant surgery, the patient inflates the expandable patient activated chamber 4 of occlusion cuff 2 by manually compressing reservoir 24 so as to reduce the volume thereof, whereby to generate increased occlusive pressures around the lumen. The compression of reservoir 24 forces the force transmitting medium outwardly therefrom and into the bulbous portion 38 of force transmitting body 36 of pressure stabilizing chamber 30 (best shown in FIG. 1). The force of the force transmitting medium is transmitted through the bulbous portion 38 and to the taper at the interface of flow control appendages 34. The force transmitting medium acts to forceably separate flow control appendages 34 to permit the movement of force transmitting medium into the patient activated tube 26 of connecting channel 22 and, subsequently, to the expandable patient activated chamber 4. When the compression of reservoir 24 is completed so that no additional force is being transmitted by the force transmitting medium through the force transmitting body 36, the natural tendency of the normally closed flow control appendages 34 to remain closed causes the appendages to again engage and seal against one another so as to prevent the movement of force transmitting medium therepast.

The inflated condition of patient activated chamber 4 is illustrated in FIG. 6. The inflation of chamber 4 causes a corresponding expansion of webbing 10. Webbing 10 has a configuration to limit the inflation of and provide chamber 4 with a relatively flat contact surface 4-1 adjacent the patient's lumen. As will be disclosed in greater detail hereinafter when referring to FIGS. 10-12, the relatively flat contact surface 4-1 of inflated patient activated chamber 4 provides for a more uniform distribution of occlusive pressures to the lumen and permits occlusion cuff 2 to be characterized by a diametric occlusion geometry, the distinct advantages of which will soon be explained.

Occasionally, however, the patient may experience a return of natural continence, such as may occur during the hours of sleep. A reduction in fluidic head pressure on the urethra (coupled with any remaining natural sphincteric function) may contribute to keeping the patient continent while in a supine position. At such times of temporarily returned continence, it may periodically become advantageous to reduce the occlusive pressures being applied to the patient's lumen by the inflated patient activated chamber 4 of occlusion cuff 2 to thereby minimize the possibility of ischemia, erosion, atrophy, and/or necrosis.

Accordingly, and continuing to refer to FIGS. 1, 5, and 6, the pressure relief ring 40 (of FIG. 1) may be manually activated, whereby to shrink chamber 4 and thereby maximize circulatory blood (or other material) flow through the lumen (e.g. urethra). More particularly, the pressure relief ring 40 is grasped between the patient's thumb and index finger so that equal and opposite omniaxial forces are applied thereto. The requirement that opposing forces be applied to pressure relief ring 40 reduces the chance that patient activated chamber 4 might be unintentionally deflated due to a sudden impact of ring 40. The opposite and omniaxial forces applied to pressure relief ring 40 are transmitted to the bulbous portion 38 of force transmitting body 36 of pressure regulating chamber 30. Therefore, force transmitting body 36 is compressed, whereby a corresponding force is generated from the bulbous portion 38 of body 36 to the arcuately shaped flow control appendages 34. Accordingly, the flow control appendages 34 are caused to rotate against one another so that the appendages are again separated to permit the movement of force transmitting medium from an inflated patient activated chamber 4 (of FIG. 6) back to the reservoir 24. More particularly, the rotation of the flow control appendages 34 moves vanes 35 in a direction transverse to the closure of appendages 34 and through the interface thereof so as to establish communication between chamber 4 and reservoir 24. Hence, the inflated patient activated chamber 4 of occlusion cuff 2 will shrink to reduce the occlusive pressures being applied to the patient's lumen and thereby minimize interference with the circulatory blood flow therethrough. The patient activated chamber 4 will return to its initial, relaxed condition (of FIG. 5) when the force transmitting medium is drained therefrom, reservoir 24 is again filled, and the patient releases his grasp of the pressure relief ring 40.

In accordance with another important feature of the present invention, and as previously disclosed when referring to FIG. 1, occlusion cuff 2 includes an inflatable physician controlled chamber 6. Thus, in the event that the patient is unable to successfully achieve post-surgical continence by expanding patient activated chamber 4, means are available only to the physician by which to variably increase the occlusive pressures generated at occlusion cuff 2 without the need for additional surgery. Thus, the physician alone may set the maximum total occlusive pressure limit to be generated by sphincter 1. That is, typical post-surgical procedure preferably requires that the sphincter 1 remain in an inactive state for a 6-8 week period. During such inactive period, a peri biomaterial tissue capsule typically forms around the occlusion cuff 2 and between cuff 2 and the patient's lumen. Such peri biomaterial tissue capsule will inherently function as a cushion between the occlusion cuff 2 and the lumen while encapsulating the cuff to minimize the likelihood of infection.

Upon completion of this period of inactivity, the patient visits his physician to test the effectiveness of implanted sphincter 1 for achieving continence. By way of example, the patient's bladder is commonly perfused with a saline solution by means of a catheter. The catheter is withdrawn and the reservoir 24 is then compressed so as to inflate patient activated chamber 4 and thereby test the effectiveness of the maximum patient initiated pressure for achieving coaptive continence in the manner already disclosed.

In the event that sufficient patient initiated occlusive pressure cannot be generated to effectively achieve coaptive continence, the physician may continuously and accurately increase the total occlusive pressures being applied to the patient's lumen (e.g. urethra). More particularly, the physician manually identifies the subcutaneous locating nodule 46 so as to ascertain the proper entry point at which to insert the tip of a syringe containing an additional supply of force transmitting medium. The syringe is then inserted into the physician circuit through nodule 46 and the conical docking port 42 of insert 32 to syringe stop 49. Physician controlled tube 28 is percutaneously infused with a minimum volume of force transmitting medium to inflate physician controlled chamber 6 (best shown in FIG. 6) until coaptive continence is achieved. The inflated condition of physician controlled chamber 6 causes a corresponding expansion of the webbing (not shown) thereof. Similar to the webbing 10 of patient activated chamber 4, the webbing is adapted to provide inflated physician controlled chamber 6 with a relatively flat contact surface 6-1 (of FIG. 6) adjacent the patient's lumen. The opposing contact surfaces 4-1 and 6-1 of the patient activated and physician controlled chambers 4 and 6, respectively, provide occlusion cuff 2 with a substantially diametric occlusion geometry for effectively and efficiently achieving coaptive continence.

By virtue of physician activated chamber 6, a back-up or redundant occlusion means is readily available without additional surgery in the event that the maximum force generated from the inflation of patient activated chamber 4 is insufficient, in itself, to achieve coaptation. Moreover, since the patient activated chamber 4 is inflated by a particular, predetermined volume of force transmitting medium from reservoir 24, the patient will be less likely to exceed the minimum pressure necessary to achieve coaptive continence. Thus, because the physician may continuously adjust the total occlusive pressures after surgery by means of physician controlled chamber 6, absolute minimum continence achieving pressures may be percutaneously set after internal tissue conditions have normalized (i.e. 6 to 8 weeks after surgery) so that the sphincter 1 can be individually tailored to the minimum occlusive pressure requirements of the patient.

As already indicated, the tightness or circumference of occlusion cuff 2 is adjusted by pulling (FIG. 7) or pushing (FIG. 9) the distal aspect 12 of cuff 2 past adjusting clip 20, such that clip 20 is received between a pair of locking ridges 14. FIG. 8 of the drawings shows occlusion cuff 2 having a circumference relative to the patient's lumen to provide an optimum symmetrical diametric occlusion geometry after chambers 4 and 6 have been activated and expanded.

Figure 7:
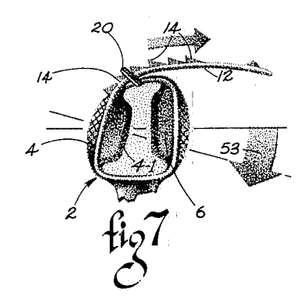
FIGS. 7-9 illustrate the preferred diametric occlusion geometry of the presently disclosed sphincter when such sphincter is adjustably secured around a lumen at various circumference settings.
Figure 8:
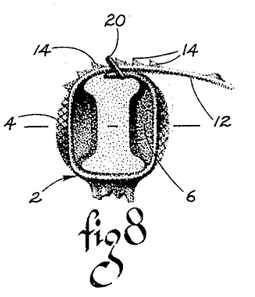

FIG. 7 of the drawings shows occlusion cuff 2 having a slightly larger circumference than that shown in FIG. 8. Nevertheless, the desired diametric occlusion geometry is substantially retained after chambers 4 and 6 have been activated and expanded, because the patient activated chamber 4 is only offset from the horizontal by a relatively small angle of less than or approximately equal to −15°. That is, the contact surface 4-1 of chamber 4 is rotated downwardly from the horizontal (in a direction indicated by arrow 53), such that a reference line aligned perpendicular to contact surface 4-1 forms an angle of approximately 15° or less with a horizontal reference line.

Figure 9:
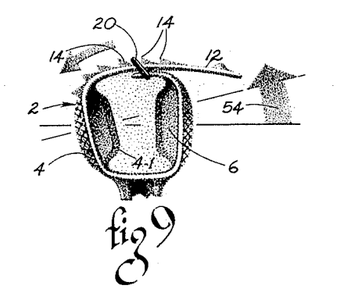

FIG. 9 of the drawings shows occlusion cuff 2 having a slightly smaller circumference than that shown in FIG. 8. The desired diametric occlusion geometry is substantially retained after chambers 4 and 6 have been activated and expanded, because the patient activated chamber 4 is again offset from the horizontal by the relatively small angle of less than or approximately equal to +15°. That is, contact surface 4-1 of chamber 4 is rotated upwardly from the horizontal (in a direction indicated by arrow 54), such that a reference line aligned perpendicular to contact surface 4-1 forms an angle of approximately 15° or less with a horizontal reference line.

Figure 10:
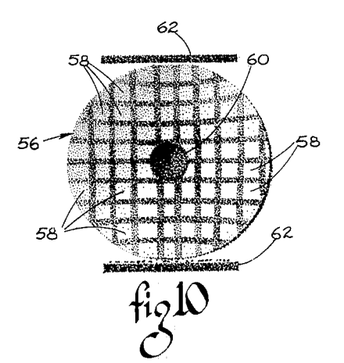
FIGS. 10 and 11 represent a simulated lumen to which is applied diametric occlusive pressures by means of two diametrically arranged test plates.
Figure 11:
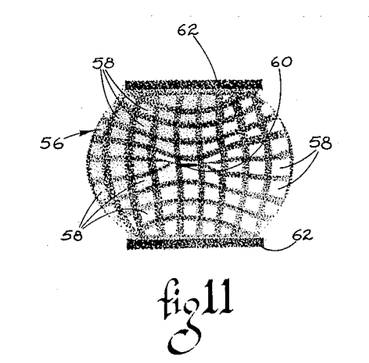

The advantages afforded by providing occlusion cuff 2 with a diametric occlusion geometry, in accordance with the present invention, is described while referring concurrently to FIGS. 10–14 of the drawings. FIG. 10 illustrates a simulated lumen 56 representative of the urethra, or the like, comprising a plurality of cells (e.g. 58) having a uniform spring constant and a passage 60 extending therethrough. Lumen 56 is shown in the opened or relaxed condition. A pair of test plates 62 are positioned to engage lumen 56 at diametrically opposing contact surfaces, corresponding to the contact surfaces 4-1 and 6-1 of patient and physician controlled chambers 4 and 6, respectively, of FIG. 6. Equal and opposite occlusive pressures are applied by test plates 62, whereby to simulate the diametric compression of lumen 56, until simulated continence is achieved (i.e. passage 60 is closed). FIG. 11 illustrates the simulated lumen 56 in the just-occluded condition after sufficient, minimal diametric compression is applied to achieve luminal closure. The resulting reduction in area of each of the cells 58 of lumen 56 is calculated under such diametric compression and the percent of area reduction is indicated, cell-by-cell, at reference numeral 63, by the histogram of FIG. 14.

Figure 12:
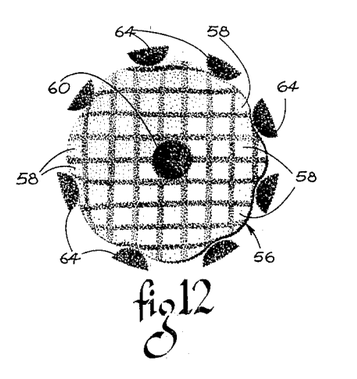
FIGS. 12 and 13 represent a simulated lumen to which is applied circumferential occlusive forces by means of circumferentially arranged test fingers.
Figure 13:
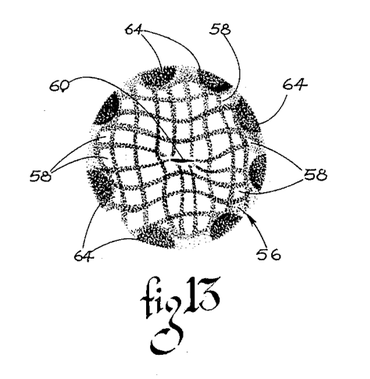

FIG. 12 illustrates the same simulated lumen 56 comprising cells 58 and passage 60 to which reference was made in FIGS. 10 and 11. A plurality of test fingers 64 are circumferentially arranged at uniformly spaced contact intervals. Occlusive pressures are applied by test fingers 64, whereby to simulate circumferential compression of lumen 56, until simulated continence is achieved and passage 60 is thereby closed. FIG. 13 illustrates the simulated lumen 56 in the just-occluded condition after sufficient, minimal circumferential compression is applied to achieve luminal closure. The resulting reduction in area of each of the cells 58 of lumen 56 is again calculated under circumferential compression and the percent of area reduction is indicated, cell-by-cell, at reference numeral 65, by the histogram of FIG. 14.

Figure 14:
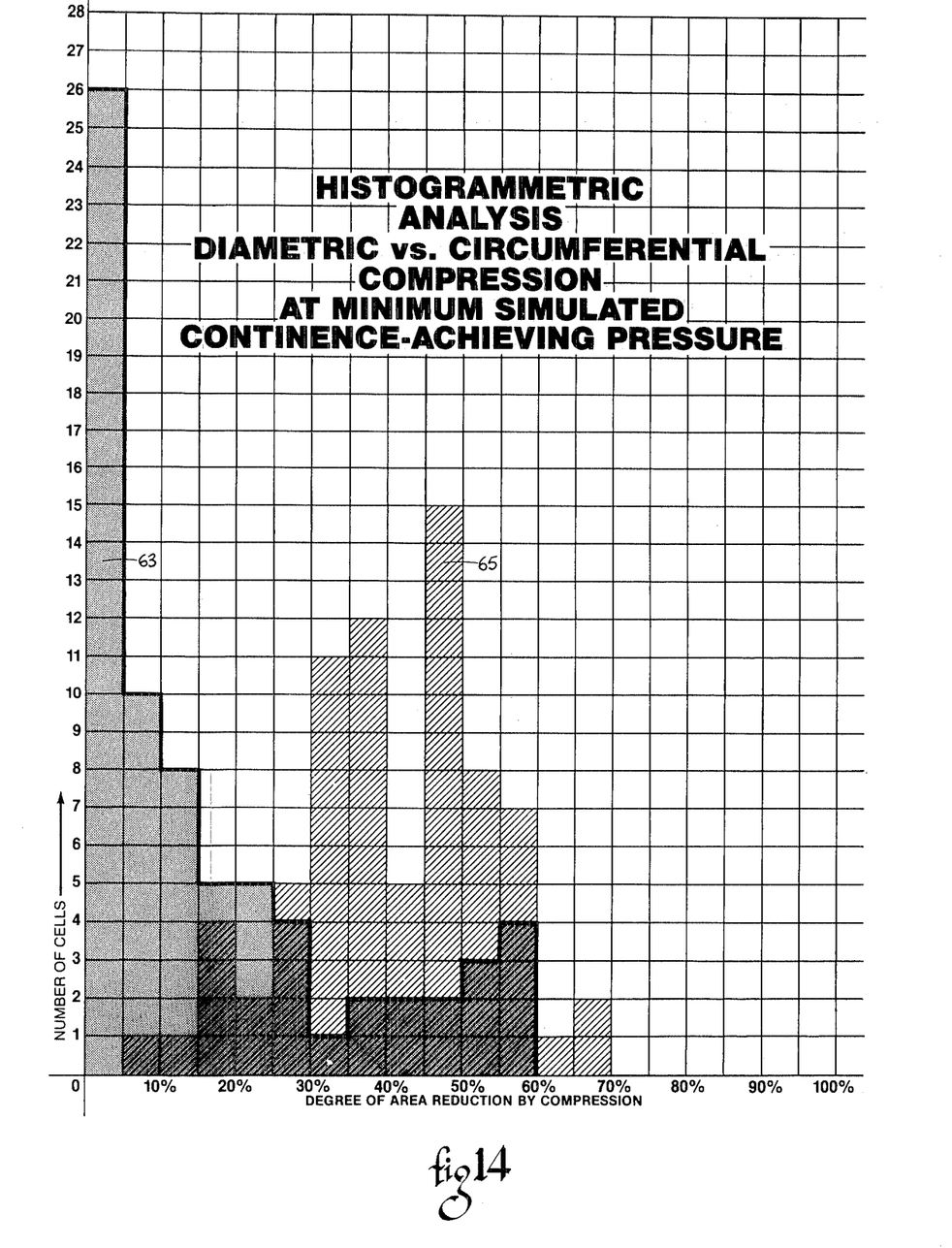
FIG. 14 illustrates a histogrammetric analysis and comparison of the diametric versus circumferential compression of the simulated lumen of FIGS. 10-13.

Referring specifically to FIG. 14 of the drawings, the results of a simulated urodynamic study, histogrammetric analysis and subsequent comparison are shown which are indicative of laboratory compression tests of the simulated lumen 56 of FIGS. 10–13. More particularly, each cell forming the lumen 56 is listed according to the percentage of area reduction caused by the respective application of the minimum diametric and circumferential pressures necessary to achieve luminal closure (i.e. occlusion of passage 60). It has been found that approximately 2.2 times more circumferential occlusive pressure, relative to diametric occlusive pressure, is necessary to achieve luminal closure. Thus, an actual lumen engaged by a sphincter which is formed in accordance with the present invention and is characterized by a diametric occlusion geometry should be less susceptible to ischemia, atrophy and ersoion while being subjected to lower mean tissue pressure. What is more, a lumen subjected to diametric compression can be expected to receive a lower maximum cell pressure than the maximum cell pressure received by a lumen subjected to circumferential compression. Moreover, a sphincter characterized by diametric compression is highly efficient (i.e. a greater number of simulated urethral cells experienced less of a reduction in area when luminal closure was achieved under diametric compression) so as to indicate a further reduction of ischemia under actual conditions. What is even more, because of the maximized sphincter efficiency under diametric compression, less force transmitting medium would be required to achieve coaptation, whereby to correspondingly reduce the maximum volume of such medium which could be accidentally discharged within the body cavity.

It will be apparent that while a preferred embodiment of the invention has been shown and described, various modifications and changes may be made without departing from the true spirit and scope of the invention. For example, it is contemplated herein to substitute a single chamber (not shown) for the previously disclosed patient activated and physician controlled chambers 4 and 6. Thus, the distal ends of each of the patient activated and physician controlled tubes 26 and 28 would be interconnected with such single chamber. As with the previously disclosed patient activated and physician controlled chambers, diametric occlusive pressures could be selectively and variably applied to a lumen by increasing the volume of force transmitting medium supplied to the single chamber by means of the patient and/or physician circuits, while providing for the same level of physician control.

Having thus set forth a preferred embodiment of the present invention, what is claimed is:

1. A prosthetic sphincter for surgical implantation to achieve coaptive continence, said sphincter including an occlusion cuff to surround at least some of a patient's lumen for applying variable occlusive pressures for occluding and relaxing the lumen and thereby controlling the movement of material therethrough, said occlusion cuff having first and second expandable chambers positioned opposite one another for engaging the patient's lumen and being adapted to receive a fluid medium to apply diametric occlusive pressures to the lumen for achieving coaptive continence when such chambers are expanded by the receipt therein of such fluid, there being no fluid communication between said first and second chambers, and said sphincter comprising first and second occlusive pressure adjustment means to be operated independently of one another and respectively interconnected with said first and second expandable chambers for supplying a selected one or the other of said chambers with fluid medium for expanding said chambers to vary the occlusive pressures being applied to the patient's lumen, said first occlusive presure adjustment means including a compressible reservoir containing a supply of said fluid medium, a first delivery tube extending between said reservoir and said first expandable chamber for delivering fluid medium to said chamber, a normally closed flow control valve to permit the movement of said fluid medium between said reservoir and said first chamber to expand said first chamber when said reservoir is compressed and said flow control valve is thereby temporarily opened, and pressure relief means location at the periphery of said flow control valve and surgically implanted so as to be manually activated to temporarily open said flow control valve to permit the movement of said fluid medium from said first chamber to said reservoir to shrink said fluid chamber, said second occlusive pressure adjustment means including a subcantaneously disposed entry port for receiving the tip of a fluid medium supplying syringe and a second delivery tube extending between said entry port and said second expandable chamber for delivering fluid medium to said second chamber to expand said second chamber when said fluid medium is injected into said entry port.

2. The prosthetic sphincter recited in claim 1, wherein each of said first and second expandable chambers includes respective expansion limiting means for causing the chambers to have substantially flat opposing contact surfaces for engaging the patient's lumens when in an expanded condition, said opposing contact surfaces applying diametric occlusive pressures to the lumen.

3. The prosthetic sphincter recited in claim 1, wherein said entry port comprises an insert having a path extending therethrough to permit the passage of fluid medium to said second delivery tube, said insert having a conical end for receiving the tip of a medium supplying syringe to be inserted through said sphincter and a tubular end for interconnection with said delivery tube.

4. The prosthetic sphincter recited in claim 3, wherein the tubular end of said insert is particularly dimensioned to stop the movement therepast of a syringe tip in order to prevent damage to said delivery tube when said tip is inserted into the conical end of said insert.

5. The prosthetic sphincter recited in claim 3, wherein a sealing gel is located within the conical end of said insert for healing a puncture formed in said sphincter when the syringe is withdrawn from said insert.

6. The prosthetic sphincter recited in claim 1, wherein said occlusion cuff includes first and second ends and fastening means for releasably connecting said first and second ends together for varying the circumference of said cuff depending upon the circumference of the patient's lumen to be surrounded.

7. The prosthetic sphincter recited in claim 6, wherein said fastening means includes a series of locking ridges at the first occlusion cuff end and a locking clip at the second occlusion cuff end, said occlusion cuff ends being releasably connected together around a patient's lumen when said locking clip is received between a pair of adjacently disposed locking ridges.

8. The prosthetic sphincter recited in claim 1, wherein said occlusion cuff includes a matrix of pressure transmitting protuberances extending in a direction for engaging the patient's lumen and transmitting occlusive pressures from said cuff to the lumen, the area of said cuff surrounding said protuberances providing regions of relatively lower occlusive pressure for maximizing blood flow and minimizing possible tissue damage.

9. The prosthetic sphincter recited in claim 1, further comprising a connecting channel enclosing the first and second delivery tubes of said first and second occlusive pressure adjustment means such that said first and second delivery tubes extend through said connecting channel for delivering fluid medium to said first and second expandable chambers.

10. The prosthetic sphincter recited in claim 9, wherein said connecting channel is helically wound and has a compression resistant cross-section for resisting kinking and a possible occlusion of said first or second delivery tubes which extend therethrough, said helically wound connecting channel having an extensible length for accommodating movement by the patient after sphincter implantation.

11. The prosthetic sphincter recited in claim 1, wherein said entry port is located at the interior of said reservoir for receipt thereat of said fluid medium supplying syringe.

* * * * *